(12) United States Patent
Zimmer et al.

(10) Patent No.: US 8,703,716 B2
(45) Date of Patent: Apr. 22, 2014

(54) MATERNAL SIALIC ACID SUPPLEMENTATION

(75) Inventors: John P. Zimmer, Boulder, CO (US); Christopher M. Butt, Erie, CO (US)

(73) Assignee: DSM IP Assets B.V., Heerlen (NL)

( * ) Notice: Subject to any disclaimer, the term of this patent is extended or adjusted under 35 U.S.C. 154(b) by 19 days.

(21) Appl. No.: 13/634,467

(22) PCT Filed: Mar. 11, 2011

(86) PCT No.: PCT/US2011/028068
§ 371 (c)(1),
(2), (4) Date: Nov. 20, 2012

(87) PCT Pub. No.: WO2011/112913
PCT Pub. Date: Sep. 15, 2011

(65) Prior Publication Data
US 2013/0137643 A1    May 30, 2013

Related U.S. Application Data

(60) Provisional application No. 61/313,630, filed on Mar. 12, 2010.

(51) Int. Cl.
*A61K 31/7012* (2006.01)

(52) U.S. Cl.
CPC .................................. *A61K 31/7012* (2013.01)
USPC ............................................ 514/20.9; 514/23

(58) Field of Classification Search
None
See application file for complete search history.

(56) References Cited

U.S. PATENT DOCUMENTS

| | | | | |
|---|---|---|---|---|
| 8,349,895 | B2 * | 1/2013 | Van Elswyk | 514/560 |
| 2004/0265462 | A1 | 12/2004 | Carlson | |
| 2007/0048354 | A1 * | 3/2007 | Wassenaar | 424/439 |

OTHER PUBLICATIONS

Wang, Bing. "Sialic Acid Is an Essential Nutrient for Brain Development and Cognition" (2009) Annu. Rev. Nutr. 29:177-222.*
Hedlund et al "N-glycolylneuraminic acid deficiency in mice: implications for human biology and evolution" (Jun. 2007) Mol Cell Biol 27(12): 4340-4346.*
Wang et al 2007 ("Dietary sialic acid supplementation improves learning and memory in piglets" (2007) Am J Clin Nutr 85: 561-569).*
Kary, Susan A. ("Effect of Dietary Glycomacropeptide and Cholesterol on Cortical Ganglioside-and Glycoprotein-bound N-acetylneuraminic acid in Young Rats" (Apr. 29, 2009) University of Kansas. p. 33).*
Mayo Foundation for Medical Education and Research. "Prenatal vitamins: Give your baby the best start" (Mar. 21, 2008) http://web.archive.org/web/20100212191156/http://www.mayoclinic.com/health/prenatal-vitamins/PR00160, Accessed Apr. 5, 2013).*
International Search Report for PCT/US2011/028068 mailed May 17, 2011.
B. Wang, "Sialic Acid is an Essential Nutrient for Brain Development and Cognition", Annu. Rev., Nutr. 2009, vol. 29:177-222: p. 187, p. 189, pp. 196-197. p. 199, p. 201, p. 211.
L. Bode, "Recent Advances on Structure, Metabolism, and Function of Human Milk Oligosaccharides", American Society for Nutrition, J. Nutr., 2006, vol. 136: 2127-2130; p. 2129 col. 2.
R. Yolken et al., "Sialic Acid Glycoproteins Inhibit in Vitro and in Vitro Replication of Rotaviruses", J. Clin. Invest., 1987, vol. 79, pp. 148-154; Abstract.
P. Gyorgy, "Biochemical Aspects", The American Journal of Clinical Nutrition, 1971, vol. 24, pp. 970-975; p. 972, col. 1, p. 973, col. 1.
Hedlund et al "N-Glycolylneuraminic Acid Deficiency in Mice: Implications for Human Biology and Evolution" Mol. Cell Biol 27(12): 4340-4346 (2007).
Briese et al 1999 Z. Geburtshilfe Neonatol 203(2): 63-68 (with English translation).
Dickson, et al, "Intestinal Neuraminidase Activity of Suckling Rats and Other Mammals," Biochem. J., 1978, 170, pp. 407-413.
European Search Report dated Jun. 11, 2013.

* cited by examiner

*Primary Examiner* — Jean C. Witz
*Assistant Examiner* — Mindy Newman
(74) *Attorney, Agent, or Firm* — Nixon & Vanderhye P.C.

(57) ABSTRACT

The invention provides methods and compositions for improving fetal and child health and development through nutritional supplementation with, for example, sialic acid. Sialic acid can be provided to a female before, during and/or after pregnancy to improve the health and development of a fetus and/or child. The sialic acid can be in a variety of forms in the supplements.

19 Claims, 16 Drawing Sheets no NANA 25 mg/kg/d NANA 50 mg/kg/d NANA 100 mg/kg/d NANA 200 mg/kg/d NANA

Ex Vivo Neurite Extension $F_{(4,325)} = 8.961, p<0.001, \beta=0.999$ $F_{(4,300)}= 2.897, p=.022, \beta=0.779$ $F_{(4,300)}= 1.158, p=0.329, \beta=0.363$

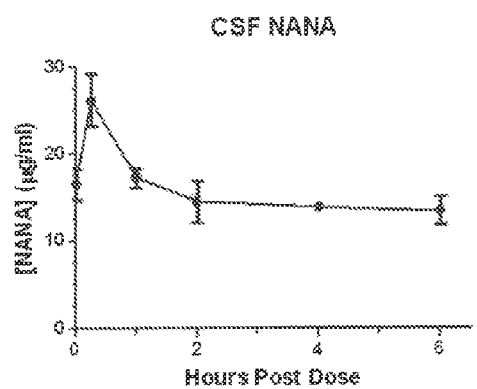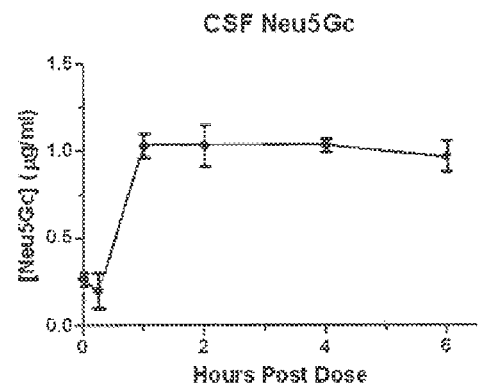
Fig. 13A
Fig. 13B

MATERNAL SIALIC ACID SUPPLEMENTATION

This application is the U.S. national phase of International Application No. PCT/US2011/028068 filed 11 Mar. 2011 which designated the U.S. and claims priority to U.S. Provisional Application No. 61/313,630 filed 12 Mar. 2010, the entire contents of each of which are hereby incorporated by reference.

BACKGROUND OF THE INVENTION

1. Field of the Invention

The invention relates to supplements containing sialic acid and the use of such supplements for a female that can result in developmental benefits for a fetus and/or child.

2. Background Art

The rapid growth and development of a fetus or child places significant demand on the maternal supply of nutrients. See, e.g., Crawford et al., Eur. J. Pediatr. 1998; 157:23-27. Nutrient deficits have profound effects on the growth and structural/functional development of the fetus or child, particularly in the growth and development of the brain. Brain growth, including cell number and structural and synaptic connectivity, reaches its peak at 26 weeks of gestation and continues at a high rate throughout the first year of life. This period of brain growth is critical because once the period has passed, it cannot be restarted. Furthermore, this period of growth is particularly important in premature infants. See, e.g., Crawford et al., Eur. J. Pediatr. 1998; 157:23-27.

Numerous studies indicate that breast-fed infants achieve better cognitive development and attain higher scores on intelligence tests than bottle-fed babies. See, e.g., Mortensen et al., JAMA 2002; 287:2365-2371. For example, intelligence quotient (IQ) has been shown to increase in infants receiving a longer duration of breastfeeding, particularly in low birth weight infants. See, e.g., Anderson et al., Am. J. Clin. Nutr. 1999; 70:525-535.

Complex lipids from gangliosides, as well as long-chain polyunsaturated fatty acids (LCPUFAs) such as docosahexaenoic acid (DHA), are present in human milk and have been implicated in the improvement of visual acuity and cognitive ability in children. See, e.g., International Publication No. WO 2009/051502 A1 and Gibson, Lancet 1999; 354:1919-1920. However, other components of human milk might be important to brain growth and development of a fetus or child. These factors, such as enzymes, hormones, growth factors, and sialic acid, are found in human milk and are typically poorly represented in infant formulas. See, e.g., McVeagh and Miller, J. Paediatr. Child Health 1997; 33:281-286.

Of the factors described above, sialic acid has been shown to have a simultaneous presence in significant amounts in both human milk and human brain. See, e.g., McVeagh and Miller, J. Paediatr. Child Health 1997; 33:281-286. Sialic acid is a generic term for the N- or O-substituted derivatives of neuraminic acid, a monosaccharide with a nine-carbon backbone, that are a structural and functional component of gangliosides. See, e.g., Varki and Schauer (2009) in Essentials of Glycobiology. $2^{nd}$ ed., Cold Spring Harbor Press. Ch. 14; and FIG. 1. The most predominant sialic acid found in mammals is N-acetylneuraminic acid (NANA).

Certain roles for sialic acid in development and disease pathology have been described. For example, inactivation of the gene encoding an enzyme of sialic acid biosynthesis, uridine diphospho-N-acetylglucosamine (UDP-GlcNAc) 2-epimerase/N-acetylmannosamine (MacNAc) kinase (GNE/MNK), has been correlated with reduced sialic acid levels and the development of hereditary inclusion body myopathy (HIBM), an adult-onset progressive neuromuscular disorder. See, e.g., Galeano et al., J. Clin. Invest. 2007; 117:1585-1594; Malicdan et al., Nature Med. 2009; 15:690-695; and Huizing and Krasnewich, Biochim. Biophys. Acta 2009; 1792:881-887. Also, inactivation of the UDP-GlcNAc/MacNAc gene has been described to result in early embryonic lethality in mice, suggesting a role for the UDP-GlcNAc/MacNAc gene in development. See, e.g., Schwarzkopf et al., PNAS 2002; 99:5267-5270. The use of sialic acid to support the immune system and re-establish central and peripheral nervous system health in the elderly has also been described. See, e.g., European Patent Application Nos. 2116140 A1 and 2116139 A1.

A mother's increased intake of some nutrients (e.g., docosahexaenoic acid) can benefit her child's brain development. However, there has been no evidence that the quantity of sialic acid a mother naturally makes is inadequate. As shown in the Examples, maternal supplementation with sialic acid clearly resulted in developmental benefits for a fetus or child, suggesting that maternal supplementation with sialic acid is needed. The present invention addresses this need by providing sialic acid which can be administered to a female during preconception, pregnancy/gestation and/or lactation/postpartum as described herein.

While maternal supplementation with NANA has not been previously described, Hedlund et al. (Mol. Cell. Biol. 2007; 27:4340-4346) reported feeding another sialic acid, N-glycolylneuraminic acid (Neu5Gc), to mice lacking the gene to produce Neu5Gc. The researchers reported that feeding Neu5Gc to dams lacking this gene does not transfer Neu5Gc to pups that also lack the gene. In addition, adult mammals are known to readily synthesize sufficient levels of sialic acid and there is no clear evidence regarding whether or not the mother supplies sialic acid to the fetus through the maternoplacental unit. See, e.g., Briese et al., Z. Geburtsh. Neonatol. 1999; 203:63-68.

The most rapid rate of brain development ("the brain growth spurt") occurs during gestation and extends to at least the end of the first year of life. As such, the present invention optimizes the developmental benefits of maternal supplements such as sialic acid for a fetus or child by providing supplementation during this critical period of brain development.

BRIEF SUMMARY OF THE INVENTION

The present invention is directed to compositions and methods for providing sialic acid to a female, comprising the administration of sialic acid to the female during at least one of the stages of preconception, pregnancy and lactation. In some embodiments, the sialic acid provides a developmental benefit to a fetus or child of the female. In some embodiments, the sialic acid is a free sialic acid. In some embodiments, the sialic acid is selected from the group consisting of: oligosaccharide conjugates, lipid conjugates, protein conjugates, and combinations thereof. In some embodiments, the sialic acid is selected from the group consisting of: 3'sialyllactose, gangliosides, and casein glycomacropeptide. In some embodiments, the sialic acid is in the form of n-acetylneuraminic acid.

In some embodiments, the sialic acid is a sialic acid precursor that is metabolized into sialic acid. In some embodiments, the sialic acid precursor is selected from the group consisting of: N-acetylmannosamine, N-propanoylmannosamine, 2-keto-3-deoxynononic acid, N-glycolylneuraminic acid, and the core sialic acid neuraminic acid molecule.

In some embodiments, the sialic acid is administered during pregnancy and lactation. In some embodiments, the sialic acid is administered during preconception, pregnancy and lactation. In some embodiments, the sialic acid is administered during about the first two years following birth.

In some embodiments, the developmental benefit is improved nervous system growth and/or development or growth of the brain of the fetus or child. In some embodiments, the developmental benefit is a neurological improvement of the brain. In some embodiments, the developmental benefit is selected from the group consisting of: increased expression and/or development of mature myelin, enhanced neurite extension, increased levels of myelin basic protein, and enhanced development the white matter of the brain. In some embodiments, the developmental benefit is in the gray matter of the brain.

In some embodiments, the sialic acid is administered to the female in a dosage form. In some embodiments, the dosage form is selected from the group consisting of: nutritional supplements, foods, pharmaceutical formulations, beverages and combinations thereof. In some embodiments, the dosage form contains sialic acid at an amount of 0.01% to 10% by weight of the dosage form. In some embodiments, the dosage form contains sialic acid at an amount of 10% to 90% by weight of the dosage form.

In some embodiments, the sialic acid is administered to the female at an amount of 5 mg/kg/day to 200 mg/kg/day of the female's body weight. In some embodiments, the sialic acid is administered at an amount of 25 mg/kg/day to 100 mg/kg/day of the female's body weight. In some embodiments, the sialic acid is administered at an amount of 20 mg/day to 4000 mg/day. In some embodiments, the sialic acid is administered at an amount of 200 mg/day to 2000 mg/day.

In some embodiments, the methods further comprise administering the sialic acid to the female in a dosage form comprising sialic acid and an excipient. An excipient can be, for example, one or more of polyunsaturated fatty acids, calcium, folic acid, vitamin E, tocotrienols, vitamin D, magnesium, phosphorus, vitamin K, iron, vitamin B12, niacin, thiamine, riboflavin, biotin, vitamin B6, and isoflavones, zinc, pantothenic acid, medium chain triglycerides, copper, manganese, magnesium, vitamin A, choline, vitamin C, iodine, selenium, prebiotics, probiotics, beta-carotene, lutein, lycopene, alpha-carotene, zeaxanthin, beta-cryptoxanthin, gamma carotene, ginger, and tryptophan.

BRIEF DESCRIPTION OF DRAWINGS/FIGURES

The present invention will be more fully understood and appreciated by the following Detailed Description in conjunction with the accompanying drawings.

FIGS. 13A-13B show NANA and Neu5Gc concentrations in cerebrospinal fluid (CSF) following NANA administration.

DETAILED DESCRIPTION OF THE INVENTION

Figure 1:
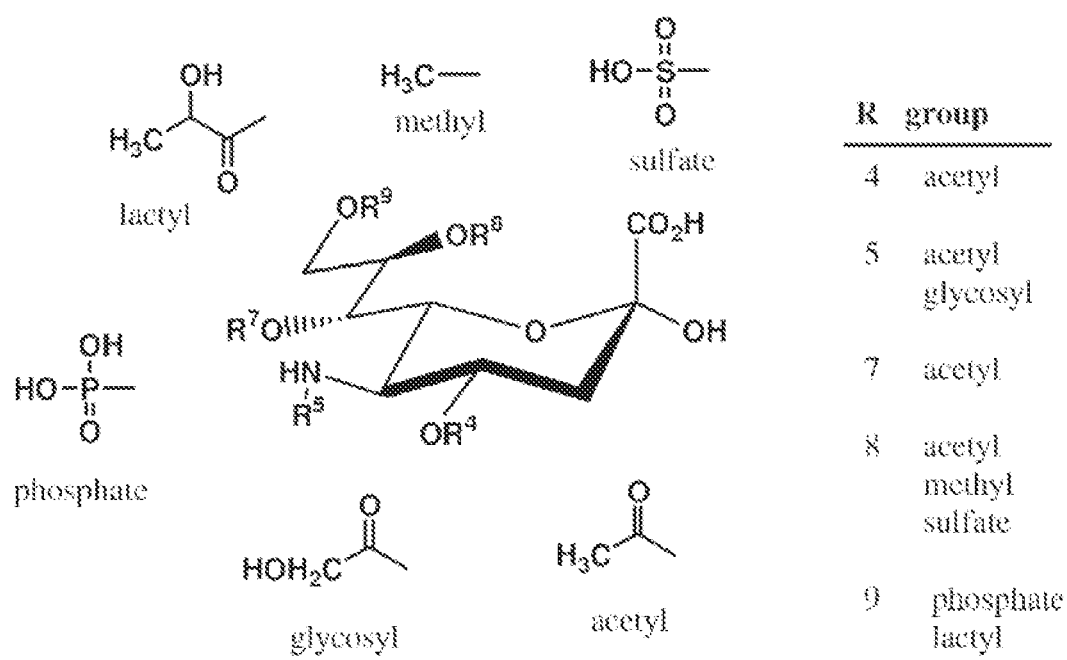
FIG. 1 is a schematic depicting members of the sialic acid family.

The present invention provides methods and compositions for improving female, fetal and/or child health and development through nutritional supplementation with, for example, sialic acid. In some embodiments, sialic acid can be administered to a female before, during and/or after pregnancy to improve the health and development of a fetus and/or child, including the developmental benefits described further herein. The sialic acid can be in a variety of forms in the supplements, including the dosage forms described further herein.

DEFINITIONS

As used herein, a "child" of the present invention, includes, but is not limited to, an individual or subject of any sex that is of an age between the time of delivery to approximately two years after delivery or to the time that breastfeeding has stopped, whichever is longer. This term includes infants and toddlers.

As used herein, a "female" of the present invention includes, but is not limited to, an individual or subject that is the biological mother of a fetus or child, a surrogate carrier of a fetus, and an individual or subject that breastfeeds a child. This term also includes an individual or subject that is attempting to become pregnant.

As used herein, a "maternal supplement" of the present invention can be administered to and useful for any female described herein.

As used herein, "breastfeeding" includes, but is not limited to, feeding from a female's breast (e.g., nursing) and feeding a child breast milk from a bottle (e.g., bottlefeeding). This includes a female who both breastfeeds and feeds infant formula to her child (e.g., partial breastfeeding).

As used herein, the term "sialic acid" refers to any member alone, or in combination with one or more other members, of the known family of derivatives of the nine-carbon sugar neuraminic acid. This term includes any sialic acid substitutions or variants and any precursors for sialic acid known in the art and described herein. This term includes conjugated and non-conjugated forms of sialic acid and free sialic acid. In some embodiments, the sialic acid is N-acetylneuraminic acid.

As used herein, "sialic acid supplementation" refers to administration of sialic acid to a female resulting in a developmental benefit for a fetus and/or child.

As used herein, a "precursor of sialic acid" or "sialic acid precursor" refers to a compound that is metabolized to form sialic acid. In embodiments, a sialic acid precursor can include, but is not limited to, N-acetylmannosamine, N-propanoylmannosamine, 2-keto-3-deoxynononic acid (KDN), N-glycolylneuraminic acid (Neu5Gc), the core sialic acid neuraminic acid molecule (Neu), and combinations thereof.

As used herein, a "developmental benefit" refers to an improvement in a factor related to the development or growth of a fetus or child. Developmental benefits of a fetus or child can include one or more of, but are not limited to, enhanced nervous system growth and/or development, neurological improvements, increased expression and/or development of mature myelin, increased neurite extension (e.g., in the hippocampus), increased levels of myelin basic protein (e.g., in the whole brain, cerebellum, corpus callosum, frontal and/or rostral corpus callosum, middle corpus callosum, midline corpus callosum decussation, lateral olfactory tract, motor output pathways, sensory input pathways, motor pyramids, and/or medial lemniscus), increased development of white matter (e.g., in the corpus callosum, lateral olfactory tract, or other white matter tracts as described above but not limited to the above), and enhanced hippocampal development, as described further herein.

As used herein, "preconception" refers to the period during which a female is attempting to become pregnant. In some embodiments, administration of sialic acid during preconception is useful for the period of time from conception to when a female realizes she is pregnant or when a pregnancy is confirmed.

As used herein, the terms "pregnancy/gestation," "pregnancy" and "gestation" refer to the period of time from conception to the delivery of a fetus. The stages of pregnancy/gestation include stage I (the first trimester), stage II (the second trimester) and stage III (third trimester).

As used herein, the terms "lactation/postpartum," "lactation" and "postpartum" refer to the period of time from the delivery of a fetus to approximately two years after delivery or to the time that breastfeeding is stopped.

Sialic Acid

Sialic acid includes a family of over 50 known derivatives of the nine-carbon sugar neuraminic acid (5-amino-3,5-dideoxy-D-glycero-D-galacto-nonulsonic acid). See, e.g., Schauer, *Glycoconj. J.* 2000; 17:485-499 and FIG. 1. As an individual compound or moiety, sialic acid is a 9 carbon amino sugar, the structure of which is readily described in the chemical literature. See, e.g., Kontou et al., *Biol. Chem.* 2009; 390:575-579. One branch of the sialic acid family is N-acetylated to form N-acetylneuraminic acid, which is the most widespread form of sialic acid in humans. See, e.g., Kontou et al., *Biol. Chem.* 2009; 390:575-579. Other generally accepted names for N-acetylneuraminic acid include sialic acid; O-Sialic acid; 5-Acetamido-3,5-dideoxy-D-glycero-D-galacto-2-nonulosonic acid; 5-Acetamido-3,5-dideoxy-D-glycero-D-galactonulosonic acid; Aceneuramic acid; N-acetyl-neuraminate; N-Acetylneuraminic acid; NANA; and Neu5Ac.

Sialic acid molecules can be substituted in more than one position, with O-substitution occurring at C4, -7, -8 and -9 (O-acetyl, O-methyl, O-sulphate, and phosphate groups) and the introduction of a double bond between C-2 and C-3 can give rise to a wide variety of possible isomers. See, e.g., Kontou et al., *Biol. Chem.* 2009; 390:575-579 and FIG. 1. Another modification is the presence of a hydroxyl group instead of an amino group at position 5 of the sugar, leading to 2-keto-3-deoxy-nonulosonic acid (KDN), which has been found in fish eggs and red blood cells. See, e.g., Kontou et al., *Biol. Chem.* 2009; 390:575-579 and Inoue et al., *J. Biol. Chem.* 1998; 273:27199-27204.

Sources of Sialic Acid

Any source of sialic acid can be used in the compositions and methods of the present invention, including, but not limited to, animal, plant and microbial sources. Exemplary sources include, but are not limited to, sialic acid in monomeric or linked forms such as monomeric N-acetylneuraminic acid or polysialic acid; sialic acid bound to a protein such as casein glycomacropeptide or mucin; sialic acid bound to a carbohydrate such as sialyllactose or sialated bacterial capsular polysaccharides; and sialic acid bound to a lipid such as a ganglioside. In some embodiments, the sialic acid is not bound to a protein, carbohydrate or lipid. In some embodiments, the sialic acid is not bound to a protein. In some embodiments, the sialic acid is not a carbohydrate. In some embodiments, the sialic acid is not bound to a lipid. In some embodiments, the sialic acid is not part of a ganglioside or other glycolipid.

In some embodiments, sialic acid can be provided by providing a precursor of sialic acid that is metabolized to sialic acid. In some embodiments, a sialic acid precursor can be N-acetylmannosamine, N-propanoylmarmosamine, 2-keto-3-deoxynononic acid (KDN), N-glycolylneuraminic acid (Neu5Gc), the core sialic acid neuraminic acid molecule (Neu), or combinations thereof. See, e.g., Kontou et al., *Biol. Chem.* 2009; 390:575-579; and Gagiannis et al., *Biochim Biophys Acta* 2007; 1770:297-306.

In some embodiments, suitable sialic acid sources can be either natural or synthetic, and can include any of the naturally occurring and currently identified sialic acid derivatives, which can include free sialic acid, oligosaccharide conjugates (e.g., sialyloligosaccharides), lipid conjugates (e.g., glycolipids), protein conjugates (e.g., glycoproteins), and combinations thereof.

In some embodiments, suitable sialic acid sources can include sialyloligosaccharides commonly found in human milk, whether natural or synthetic. In some embodiments, the sialyloligosaccharides can be 3'sialyllactose (3'SL) and/or 6'sialyllactose (6'SL). Other suitable sialyloligosaccharides include, but are not limited to, those that contain one or more sialic acid molecules conjugated to oligosaccharides.

Other suitable sialic acids for use herein include, but are not limited to, any corresponding glycolipid that is also suitable for use in an infant formula, including, but not limited to, sphingosine, glucose, galactose, N-acetylgalactosamine, N-acetylglucosamine, and N-acetylneuraminic acid molecule. Such sialic acid compounds can also include, but are not limited to, any one or more of the several glycoproteins commonly found in human milk that are known to be sialylated (e.g., kappa-casein, alpha-lactalbumin, and lactoferrin).

In some embodiments, suitable sources of sialic acid can include isolates, concentrates, and/or extracts of mammalian milk or milk products, including, but not limited to, human and bovine milk. In some embodiments, bovine milk can be a source for use herein, including, but not limited to, enriched whey protein concentrates as described herein. In some embodiments, individual sources of sialic acid suitable for use herein can include, but are not limited to, Lacprodan CGMP-10 (casein glycomacropeptide with 4.2% sialic acid), available from Aria Food Ingredients, Denmark; and Biopure glycomacropeptide (with 7-8% sialic acid), available from Davisco Foods International, Eden Prairie, Minn., USA.

Dosage Forms

In some embodiments, sialic acid can be administered to a female in a composition or dosage form such as a nutritional supplement, food, pharmaceutical formulation, beverage or combinations thereof. In some embodiments, a dosage form is a food, beverage and/or nutritional supplement. In some embodiments, the dosage form is a food and/or beverage. In some embodiments, the dosage form is a food. In some embodiments, the dosage form is a nutritional supplement, including, but not limited to a prescription or nonprescription maternal prenatal vitamin. The preparations of such dosage forms are well known to persons of ordinary skill in the art.

In some embodiments, a sialic acid can be administered in a pharmaceutical formulation. Examples of such pharmaceutical formulations include, but are not limited to, the dosage form is a chewable tablet, quick dissolve tablet, effervescent tablet, reconstitutable powder, elixir, liquid, solution, suspension, emulsion, tablet, multi-layer tablet, bi-layer tablet, capsule, soft gelatin capsule, hard gelatin capsule, caplet, lozenge, chewable lozenge, bead, powder, granule, particle, microparticle, dispersible granule, cachet, douche, suppository, cream, topical, inhalant, aerosol inhalant, patch, particle inhalant, implant, depot implant, ingestible, injectable, infusion, health bar, confection, cereal, cereal coating, nutritive food, functional food and/or combinations thereof. The preparations of such pharmaceutical formulations are well known to persons of ordinary skill in the art.

In some embodiments, the dosage form is a baked good and/or mix; chewing gum; breakfast cereal; cheese product; nut and/or nut product; gelatin, pudding, and/or filling; frozen dairy product; milk product; dairy product; soft candy; soup and/or soup mix; snack food; fruit juice; vegetable juice; fat and/or oil; fish product; plant protein product; poultry product; and/or meat product. In some embodiments, the dosage form is a confectionary (e.g., chocolate) and/or fortified bar. The preparations of such dosage forms are well known to persons of ordinary skill in the art.

Sialic Acid Administration and Dosages

The amount of sialic acid in a dosage form can vary according to factors such as the disease state, age, sex, and weight of the individual or female. Dosage regimens can be adjusted to provide an optimum sialic acid supplementation and/or developmental benefit. Dosage regimens can also be adjusted to contain varying levels of one or more sialic acid. In some embodiments, the varying levels of sialic acid can be adapted for each stage of preconception, pregnancy or postpartum. The specification for the dosage forms of the present invention can be dictated by or directly dependent on, for example, the unique characteristics of a particular sialic acid and the particular developmental benefit to be achieved.

In some embodiments, a dosage form useful in the methods of the invention can contain sialic acid in an amount of at least 0.01%, at least 0.1%, at least 0.2%, at least 0.3%, at least 0.4%, at least 0.5%, at least 0.6%, at least 0.7%, at least 0.8%, at least 0.9%, at least 1.0%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or at least 99.5% by weight of the dosage form, and useful ranges can be selected between any of these values, e.g., from 0.01% to 99%, 0.01% to 1%, 0.1% to 10%, 0.5% to 10%, 1% to 5%, 5% to 25%, 5% to 95%, 5% to 80%, 10% to 95%, 15% to 95%, 20% to 95%, 25% to 95%, 30% to 95%, 35% to 95%, 40% to 95%, 45% to 95%, 50% to 95%, 1% to 99%, 5% to 99%, 10% to 99%, 15% to 99%, 20% to 99%, 25% to 99%, 30% to 99%, 35% to 99%, 40% to 99%, 45% to 99%, 50% to 99%, 5% to 70%, 10% to 70%, 15% to 70%, 20% to 70%, 25% to 70%, 30% to 70%, 35% to 70%, 40% to 70%, 45% to 70%, and 50% to 70% by weight of the dosage form.

In some embodiments, a dosage form useful in the methods of the invention can contain sialic acid in an amount of 0.01% to 20% by weight of the dosage form and, for example, can be a food and/or beverage. In some embodiments, a dosage form can contain sialic acid in an amount of 0.1% to 10% by weight of the dosage form and, for example, can be a food and/or beverage. In some embodiments, a dosage form can contain sialic acid in an amount of 1% to 5% by weight of the dosage form and, for example, can be administered in a food and/or beverage. In some embodiments, a dosage form can contain sialic acid in an amount of 0.01% to 1% by weight of the dosage form and, for example, can be administered in a food and/or beverage. In some embodiments, a dosage form can contain sialic acid in an amount of 0.01% to 99% by weight of the dosage form and, for example, can be administered in a food and/or beverage.

In some embodiments, a dosage form useful in the methods of the invention can contain sialic acid in an amount of 10% to 90% by weight of the dosage form and, for example, can be a nutritional supplement. In some embodiments, a dosage form can contain sialic acid in an amount of 20% to 80% by weight of the dosage form and, for example, can be a nutritional supplement. In some embodiments a dosage form can contain sialic acid in an amount of 30% to 70% by weight of the dosage form and, for example, can be a nutritional supplement. In some embodiments, a dosage form can contain sialic acid in an amount of 40% to 60% by weight of the dosage form and, for example, can be a nutritional supplement. In some embodiments, a dosage form can contain sialic acid in an amount of 70% to 90% by weight of the dosage form and, for example, can be a nutritional supplement. In some embodiments, a dosage form can contain sialic acid in an amount of 0.1% to 99% by weight of the dosage form and, for example, can be a nutritional supplement.

In some embodiments, the amount of sialic acid useful in the methods of the invention can be at least 2 mg/kg/day, at least 3 mg/kg/day, at least 5 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, at least 50 mg/kg/day, at least 55 mg/kg/day, at least 60 mg/kg/day, at least 65 mg/kg/day, at least 70 mg/kg/day, at least 75 mg/kg/day, at least 80 mg/kg/day, at least 85 mg/kg/day, at least 90 mg/kg/day, at least 95 mg/kg/day, at least 100 mg/kg/day, at least 105 mg/kg/day, at least 110 mg/kg/day, at least 115 mg/kg/day, at least 120 mg/kg/day, at least 125 mg/kg/day, at least 130 mg/kg/day, at least 135 mg/kg/day, at least 140 mg/kg/day, at least 145 mg/kg/day, at least 150 mg/kg/day, at least 155 mg/kg/day, at least 160 mg/kg/day, at least 165 mg/kg/day, at least 170 mg/kg/day, at least 175 mg/kg/day, at least 180 mg/kg/day, at least 185 mg/kg/day, at least 190 mg/kg/day, at least 195 mg/kg/day, or at least 200 mg/kg/day of the female's body weight, and useful ranges can be selected between any of these values, e.g., from 2 mg/kg/day to 200 mg/kg/day, 3 mg/kg/day to 200 mg/kg/day, 5 mg/kg/day to 200 mg/kg/day, 10 mg/kg/day to 175 mg/kg/day, 25 mg/kg/day to 150 mg/kg/day, 50 mg/kg/day to 100 mg/kg/day, 5 mg/kg/day to 75 mg/kg/day, 10 mg/kg/day to 75 mg/kg/day, 3 mg/kg/day to 50 mg/kg/day, and 25 mg/kg/day to 50 mg/kg/day.

In some embodiments, the amount of sialic acid useful in the methods of the invention can be at least 20 mg/day, at least 25 mg/day, at least 30 mg/day, at least 35 mg/day, at least 40 mg/day, at least 45 mg/day, at least 50 mg/day, at least 55 mg/day, at least 60 mg/day, at least 70 mg/day, at least 75 mg/day, at least 80 mg/day, at least 85 mg/day, at least 90 mg/day, at least 100 mg/day, at least 110 mg/day, at least 120 mg/day, at least 125 mg/day, at least 130 mg/day, at least 140 mg/day, at least 150 mg/day, at least 160 mg/day, at least 170 mg/day, at least 175 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, at least 1000 mg/day, at least 1100 mg/day, at least 1200 mg/day, at least 1300 mg/day, at least 1400 mg/day, at least 1500 mg/day, at least 1600 mg/day, at least 1700 mg/day, at least 1800 mg/day, at least 1900 mg/day, at least 2000 mg/day, at least 2100 mg/day, at least 2200 mg/day, at least 2300 mg/day, at least 2400 mg/day, at least 2500 mg/day, at least 2600 mg/day, at least 2700 mg/day, at least 2800 mg/day, at least 2900 mg/day, at least 3000 mg/day, at least 3100 mg/day, at least 3200 mg/day, at least 3300 mg/day, at least 3400 mg/day, at least 3500 mg/day, at least 3600 mg/day, at least 3700 mg/day, at least 3800 mg/day, at least 3900 mg/day, or at least 4000 mg/day, and useful ranges can be selected between any of these values, e.g., from 20 mg/day to 4000 mg/day, 50 mg/day to 3000 mg/day, 75 mg/day to 2000 mg/day, 100 mg/day to 1000 mg/day, 200 mg/day to 2000 mg/day, 250 mg/day to 1500 mg/day, 100 mg/day to 500 mg/day, 250 mg/day to 2000 mg/day, 200 mg/day to 1000 mg/day, or an amount that is not less than 200 mg/day.

In some embodiments, sialic acid can be administered during one or more of the stages of preconception, pregnancy/gestation and during lactation/postpartum. In some embodiments, sialic acid can be administered during a stage of pregnancy/gestation. In some embodiments, sialic acid can be administered during stage I of pregnancy/gestation (the first trimester), stage II of pregnancy/gestation (the second trimester), and/or stage III of pregnancy/gestation (third trimester). In some embodiments, sialic acid can be administered during preconception, stage I of pregnancy/gestation (the first trimester), stage II of pregnancy/gestation (the second trimester), stage III of pregnancy/gestation and/or during lactation/postpartum. In other embodiments, sialic acid can be administered during the first, second and/or third trimester and/or during lactation/postpartum. In other embodiments, sialic acid can be administered during the first, second, and/or third trimester. In some embodiments, sialic acid is administered can be administered during each stage of pregnancy. In some embodiments, sialic acid is administered continuously throughout each stage of pregnancy.

In some embodiments, sialic acid can be administered during preconception and/or the first trimester. In some embodiments, sialic acid can be administered during the second trimester. In some embodiments, sialic acid can be administered during the third trimester. In some embodiments, sialic acid can be administered during lactation/postpartum. In some embodiments, sialic acid can be administered postpartum to the female during the first two years following birth.

In some embodiments, a fetus is exposed to sialic acid by administration of sialic acid to a female pregnant with the fetus. In some embodiments, sialic acid supplementation can have benefits for the female even if the female is not breast feeding a child. In some embodiments, a sialic acid can be administered to the female and to a fetus or child. In some embodiments, a fetus is exposed to sialic acid by administration of sialic acid to the biological mother of the fetus. In some embodiments, a fetus is exposed to sialic acid by administration of sialic acid to a surrogate carrier of the fetus. In some embodiments, the fetus is exposed to sialic acid during the first, second and third trimesters of pregnancy. In some embodiments, the fetus is exposed to sialic acid during the first and second trimesters of pregnancy. In some embodiments, the fetus is exposed to sialic acid during the second and third trimesters of pregnancy. In some embodiments, the fetus is exposed to sialic acid during the first and third trimesters of pregnancy. In some embodiments, the fetus is exposed to sialic acid during the first trimester of pregnancy. In some embodiments, the fetus is exposed to sialic acid during the second trimester of pregnancy. In some embodiments, the fetus is exposed to sialic acid during the third trimester of pregnancy.

In some embodiments, a child is exposed to sialic acid by feeding the child an infant formula containing sialic acid. In some embodiments, a child is exposed to sialic acid by feeding the child breast milk containing sialic acid, wherein the breast milk is from a female receiving sialic acid supplementation as described herein. In some embodiments, a child is exposed to sialic acid by feeding the child breast milk containing sialic acid, wherein the breast milk is from the biological mother of the child receiving sialic acid supplementation as described herein. In some embodiments, a child is exposed to sialic acid by feeding the child breast milk containing sialic acid, wherein the breast milk is from the surrogate carrier of the child receiving sialic acid supplementation as described herein. In some embodiments, the child is exposed to sialic acid from birth to 5 years of age. In some embodiments, the child is exposed to sialic acid from birth to 4 years of age. In some embodiments, the child is exposed to sialic acid from birth to 3 years of age. In some embodiments, the child is exposed to sialic acid from birth to 2 years of age. In some embodiments, the child is exposed to sialic acid from birth to 1 year of age. In some embodiments, the child is exposed to sialic acid from 1 to 3 years of age. In some embodiments, the child is exposed to sialic acid from 1 to 2 years of age.

In some embodiments, sialic acid can be provided on a daily basis during all or most of the period of time from birth to about 24 months of age. In some embodiments, sialic acid can be provided on less than a daily basis for a time period of less than two years, as long as desirable results are obtained. In some embodiments, sialic acid can be administered to the female beginning in the first trimester, continuing throughout gestation, and during about the first two years of lactation/breastfeeding following birth.

In some embodiments, a dosage form comprises sialic acid and one or more excipients. In some embodiments, an excipient can be, for example, one or more additional nutritional supplements and/or maternal prenatal vitamins, including, but not limited to, one or more polyunsaturated fatty acids, calcium, folic acid, vitamin E, tocotrienols, vitamin D, magnesium, phosphorus, vitamin K, iron, vitamin B12, niacin, thiamine, riboflavin, biotin, vitamin B6, and isoflavones, zinc, pantothenic acid, medium chain triglycerides, copper, manganese, magnesium, vitamin A, choline, vitamin C, iodine, selenium, prebiotics, probiotics, beta-carotene, lutein, lycopene, alpha-carotene, zeaxanthin, beta-cryptoxanthin, gamma carotene, ginger, and tryptophan.

In some embodiments, a composition or dosage form of the invention comprises sialic acid. In some embodiments, a composition or dosage form of the invention comprises sialic acid and infant formula. In some embodiments, a dosage form can comprise at least 0.1 mg, at least 1 mg, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 200 mg, at least 250 mg, at least 300 mg, at least 350 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, at least 1,000 mg, at least 1,100 mg, at least 1,200 mg, at least 1,300 mg, at least 1,400 mg, at least 1,500 mg, at least 1,600 mg, at least 1,700 mg, at least 1,800 mg, at least 1,900 mg, or at least 2,000 mg of sialic acid, and useful ranges can be selected between any of these values, e.g., from 0.1 mg to 2,000 mg of sialic acid, 1 mg to 1,000 mg, 1 mg to 500 mg, 1 mg to 100 mg of sialic acid, 5 mg to 50 mg of sialic acid, 10 mg to 40 mg, or 25 mg to 1,000 mg of sialic acid.

In some embodiments, a dosage form is administered to the female at least once a day, at least twice a day, at least three times a day, at least four times a day, at least five times a day, at least six times a day, at least seven times a day, at least eight times a day, at least nine times a day, or at least ten times a day. In some embodiments, a dosage form is administered to the female from once to ten times a day. In some embodiments, a dosage form is administered to the female from once to five times a day. In some embodiments, a dosage form is administered to the female from one to three times a day.

Benefits of Sialic Acid Supplementation

In some embodiments, a female in preconception, pregnancy/gestation or lactation/postpartum receiving sialic acid supplementation can realize developmental benefits for a fetus and/or child. In some embodiments, the developmental benefit can be improved nervous system growth and/or development or growth of the brain. In some embodiments, the developmental benefit can be improved cognitive performance, earlier attainment of normal cognitive skills, improved motor skills, or earlier attainment of normal motor skills. In some embodiments, the developmental benefit can be a structural improvement in the brain that can include, but is not limited to, one of more of the following: increased expression and/or development of mature myelin, enhanced neurite extension, increased levels of myelin basic protein at earlier developmental timepoints, and enhanced development of the white matter of the brain. In some embodiments, an increased thickness of the myelin sheath and increased electrical conduction velocities can occur. In some embodiments, the white matter can be the corpus callosum, the lateral olfactory tract, the motor pyramids, the medullary pyramids, and/or the pyramids, but any or all white matter regions of the brain can be involved. In some embodiments, the developmental benefit can be enhanced development of the brain's hippocampus, which can include increased connectivity between brain cells, greater numbers of synapses, greater cell numbers, or longer cell survival times, but enhancement of these measures can be in any gray matter region of the brain (e.g., cerebral cortex, cerebellum, and all known nuclei of the brain). Methods for determining the developmental benefits are well known to persons of ordinary skill in the art (e.g., Calderon and Kim, *J. Neurochem.* 2004; 90:979-988; Donarum et al., *J. Inherit. Metab. Dis.* 2006; 29:143-156; Moriguchi and Salem, *J. Neurochem.* 2003; 87: 297-309) and described, for example, in the Examples.

In some embodiments, a developmental benefit is increased neurite extension (e.g., hippocampal) in the brain of the child or fetus. In some embodiments, neurite extension with sialic acid supplementation is increased by at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 45%, at least 50%, at least 55%, at least 60%, at least 65%, at least 70%, at least 75%, at least 80%, at least 85%, at least 90%, or at least 100% compared to neurite extension without sialic acid supplementation. Useful ranges can be selected between any of these values, e.g., neurite extension with sialic acid supplementation can be increased from 0.01% to 100%, 0.01% to 75%, 0.01% to 50%, 1% to 50%, 5% to 50%, 10% to 50%, 0.01% to 10%, 0.01% to 5%, 0.01% to 1%, 0.01% to 0.5%, 0.01% to 0.2% or 0.1% to 0.2%, compared to neurite extension without sialic acid supplementation. In some embodiments, increased neurite extension is measured by immunocytochemistry for the neuron-specific marker, Map2a. In some embodiments, increased neurite extension results from the administration of sialic acid to the female during preconception and/or pregnancy. In some embodiments, increased neurite extension results from the administration of sialic acid to the female during lactation. In some embodiments, increased neurite extension results from the administration of sialic acid to the female during pregnancy and not during lactation. In some embodiments, increased neurite extension results from the administration of sialic acid to the female during lactation and not during pregnancy.

In some embodiments, a developmental benefit is increased levels of myelin basic protein (MBP) in the brain of the child or fetus. In some embodiments, MBP expression in the brain (e.g., whole brain, cerebellum, corpus callosum, frontal and/or rostral corpus callosum, middle corpus callosum, midline corpus callosum decussation, lateral olfactory tract, motor output pathways, sensory input pathways, motor pyramids, and/or medial lemniscus) with sialic acid supplementation is increased by at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 45%, at least 50%, at least 55%, at least 60%, at least 65%, at least 70%, at least 75%, at least 80%, at least 85%, at least 90%, at least 100% compared to MBP expression without sialic acid supplementation. Useful ranges can be selected between any of these values, e.g., MBP expression with sialic acid supplementation can be increased by 0.01% to 100%, 0.01% to 25%, 0.1% to 25%, 1% to 25%, 1% to 20%, 1% to 10%, 1% to 5%, or 5% to 20% compared to MBP expression without sialic acid supplementation. In some embodiments, MBP expression is measured by immunocytochemistry.

In some embodiments, increased MBP expression results from the administration of sialic acid to the female during preconception and/or pregnancy. In some embodiments, increased MBP expression results from the administration of sialic acid to the female during lactation. In some embodiments, increased MBP expression results from the administration of sialic acid to the female during pregnancy and not during lactation. In some embodiments, increased MBP expression results from the administration of sialic acid to the female during lactation and not during pregnancy.

In some embodiments, MBP expression with sialic acid supplementation is increased in the corpus callosum, rostral corpus callosum, midline corpus callosum, lateral olfactory tract and/or midline corpus callosum decussation compared to MBP expression without sialic acid supplementation. In some embodiments, MBP expression with sialic acid supplementation is increased in the corpus callosum, rostral corpus callosum, midline corpus callosum, lateral olfactory tract and/or midline corpus callosum decussation, and is not increased in the motor output pathways, sensory input pathways, motor pyramids and/or medial lemniscus compared to MBP expression without sialic acid supplementation. In some embodiments, MBP expression with sialic acid supplementation is increased in the corpus callosum, rostral corpus callosum, midline corpus callosum, lateral olfactory tract and/or midline corpus callosum decussation, and is not increased in the motor output pathways, sensory input pathways, motor pyramids and/or medial lemniscus compared to MBP expression without sialic acid supplementation, and the sialic acid is administered to the female during pregnancy. In some embodiments, MBP expression with sialic acid supplementation is increased in the corpus callosum, rostral corpus callosum, midline corpus callosum, lateral olfactory tract and/or midline corpus callosum decussation, and is not increased in the motor output pathways, sensory input pathways, motor pyramids and/or medial lemniscus compared to MBP expression without sialic acid supplementation, and the sialic acid is administered to the female during pregnancy and not during lactation.

In some embodiments, MBP expression with sialic acid supplementation is increased in the cerebellum compared to MBP expression without sialic acid supplementation. In some embodiments, MBP expression with sialic acid supplementation is increased in the cerebellum compared to MBP expression without sialic acid supplementation, and the sialic acid is administered during lactation. In some embodiments, MBP expression with sialic acid supplementation is increased in the cerebellum compared to MBP expression without sialic acid supplementation, and the sialic acid is administered during lactation and not during pregnancy.

In some embodiments, the sialic acid administered to a female at least in part crosses the blood brain barrier. In some embodiments, the sialic acid administered to a female is N-acetylneuraminic acid (NANA), which at least in part crosses the blood brain barrier. In some embodiments, the sialic acid administered to a female is NANA, which at least in part is converted into Neu5Gc in non-human animals. In some embodiments, the sialic acid administered to a female is NANA, which at least in part crosses the blood brain barrier and is at least in part converted into Neu5Gc in non-human animals.

In some embodiments, the sialic acid administered to a female is present in the cerebrospinal fluid (CSF). In some embodiments, the sialic acid administered to a female is NANA, and the NANA is present at least in part in the CSF. In some embodiments, the sialic acid administered to a female is NANA, and the NANA is at least in part converted into Neu5Gc in non-human animals. In some embodiments, the sialic acid administered to a female is NANA, and the NANA is present at least in part in the CSF and is at least in part converted into Neu5Gc in non-human animals.

In some embodiments, the invention relates to the use of any of the sialic acid compositions described herein in the preparation of a dosage form for any of the uses described herein.

Additional objects, advantages, and novel features of this invention will become apparent to those skilled in the art upon examination of the following examples thereof, which are not intended to be limiting.

EXAMPLES

Example 1

Maternal NANA Supplementation Protocol

To determine the effects of supplementing maternal diets with sialic acid (n-acetylneuraminic acid; NANA) on the brain development of the offspring, forty (40) pregnant Long-Evans rats were placed on four (4) diets (10 dams per diet) that differed in their administration of sialic acid (Nacalai, San Diego, Calif.). All animals were started on the diets on the $4^{th}$ day after being mated (gestational day 4).

Figure 2:
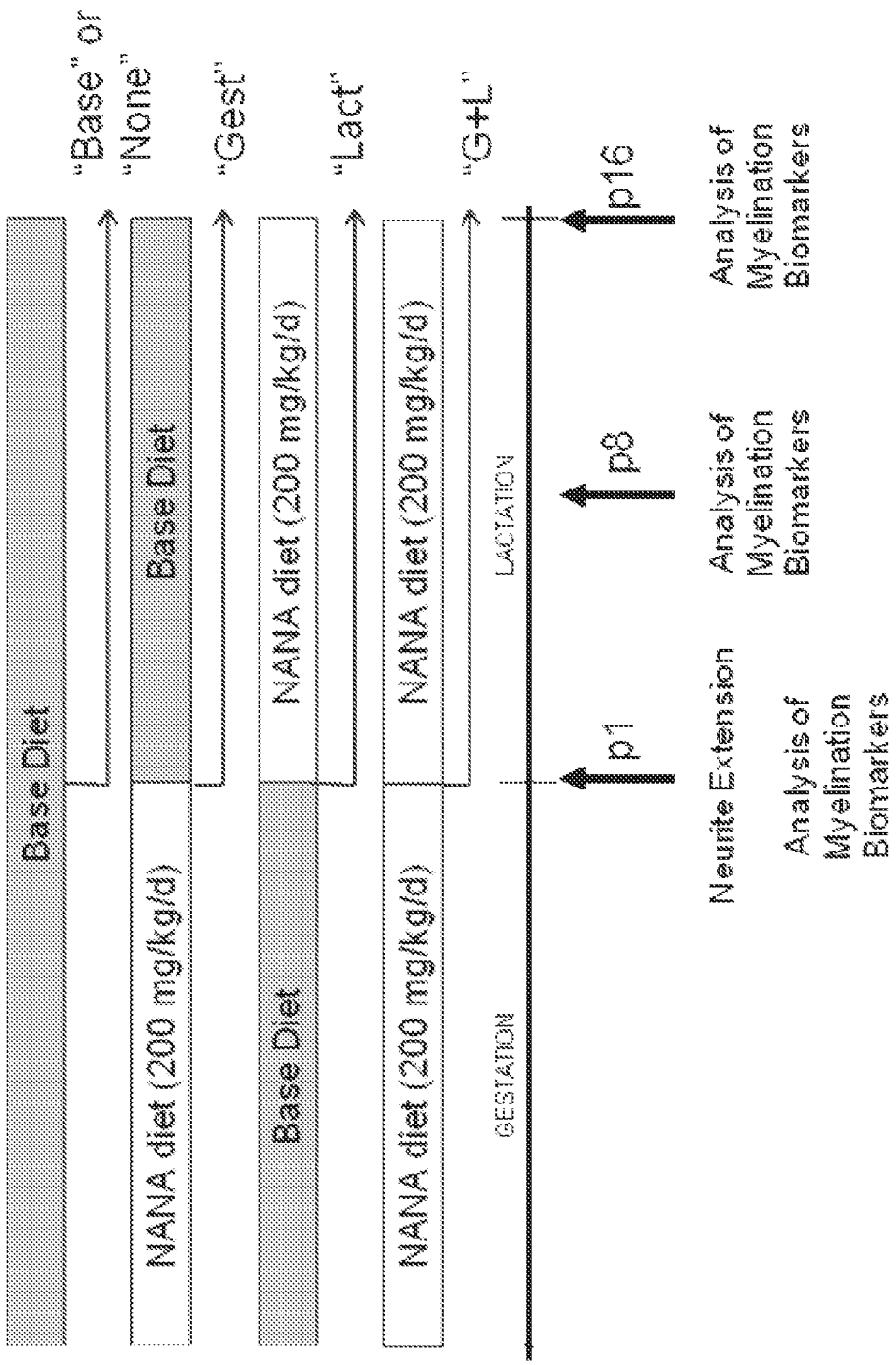
FIGS. 2 and 3A-3B show the dietary regimens of rats receiving sialic acid-supplemented diets, the effects of which are described in the Examples.

As shown in FIG. 2, control animals were placed on a base diet ("Base" or "None") which contained no detectable amounts of NANA throughout gestation and lactation. Dams placed on the gestational diet ("Gest") received NANA (200 milligrams (mg) per kilogram (kg) body weight per day (d)) only during gestation. These animals were then placed on a base diet after the offspring were born. Conversely, dams on the lactational diet ("fact") were placed on the base diet during gestation but received NANA (200 mg/kg/d) through the diet during lactation. Dams receiving NANA (200 mg/kg/d) through the diet throughout gestation and lactation were known as the "G+L" group.

FIG. 2 also shows how and when the offspring were used to determine the effects of the maternal diets on offspring development. After birth, the pups born to each diet group were crossfostered within their respective group to control for any differences in maternal care. The litters were then culled to 10 pups per dam to prevent nutritional differences caused by lack of access to the dam. The study was also designed to allow for the use of 5 pups at each endpoint (N=5) while keeping the litter size equal across all groups. Pups were taken at postnatal day 1 (p1) to determine potential differences between gestational supplementation and lactational supplementation of the maternal diet. Pups were taken at postnatal day 16 (p16) because they begin to access the mother's food directly at p18, which would preclude any assessment of maternal transfer of NANA to the pups. Pups were also taken at p8 because it served as a midway timepoint and because the primary biomarker used cannot be detected until this day in rat development.

Figure 3A:
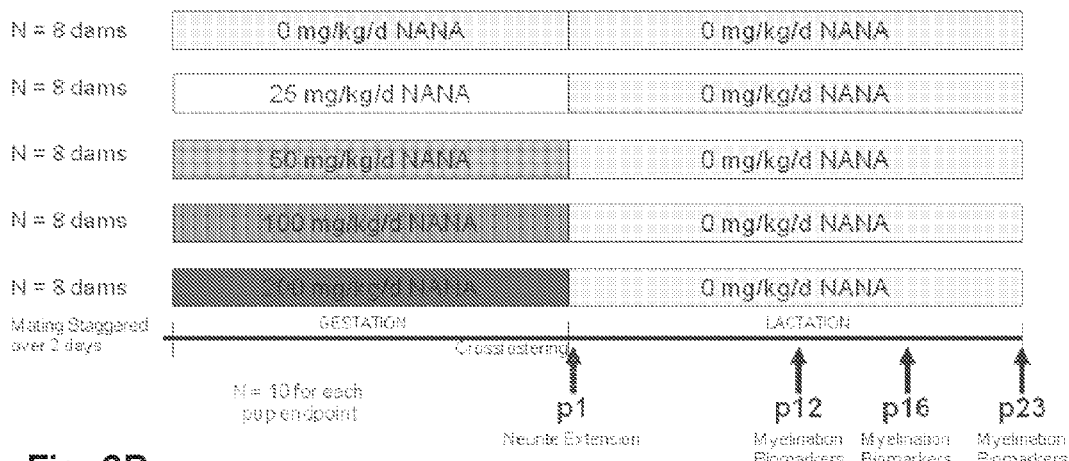
Figure 3B:
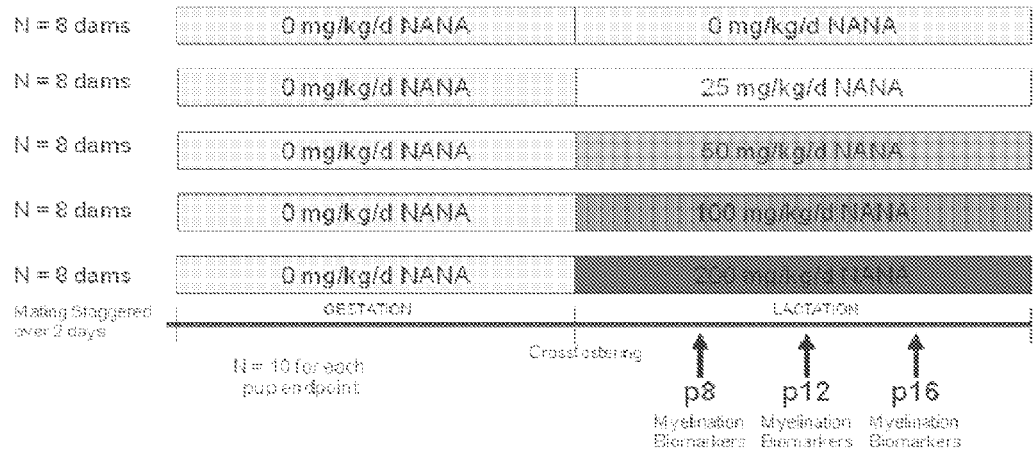

FIGS. 3A and 3B show the maternal NANA supplementation protocol for experiments testing additional doses of NANA administered during gestation (FIG. 3A) and lactation (FIG. 3B).

As described in the following examples, three major endpoints were used in this study: myelin basic protein (MBP) expression in the developing whole brain, ex vivo neurite extension of neurons cultured from the hippocampus, and assessment of the thickness of MBP expression in the developing brain Example 2

Maternal Feeding of NANA During Gestation and Lactation Enhances the Expression of MBP in Offspring MBP expression is a measure of brain development because it is a specific measure of the degree of mature myelination of the brain's circuitry. Myelin is the insulation between the "wires" of the brain and decreases electrical resistance in the brain's circuits much in the same way that insulation decreases electrical resistance in copper wiring. Decreased resistance allows for better signaling and subsequent developmental differentiation. Thus, the expression levels of mature myelin are associated with brains that are farther along in development.

Figures 4A, 4B:
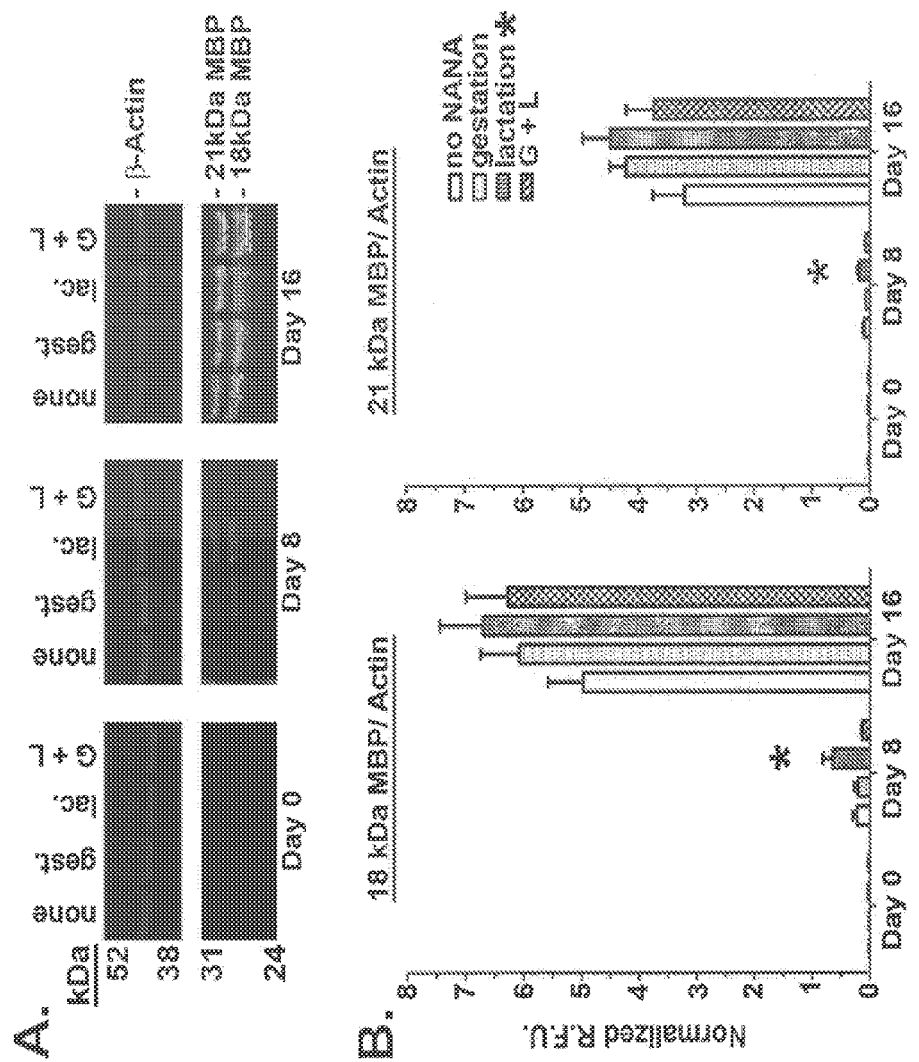
FIGS. 4A-4B show the effects of maternal sialic acid supplementation on the expression of myelin basic protein (MBP), normalized to β-actin expression, in the brains of the developing offspring (rat).

To determine the effects of maternal NANA supplementation on the brain development of offspring, MBP expression was measured by western blot analysis of whole brain lysates that were harvested from pups at postnatal days 0, 8, and 16 described in FIG. 2. As shown in FIG. 4A, the blots were probed with an antibody for MBP (lower panels; Millipore, Billerica, Mass. or Covance, Princeton, N.J.) that recognizes two distinct isoforms (18 and 21 kilodaltons [kDa] in molecular weight). The blots were also probed with an antibody for β-actin (upper panels; Cell Signaling Technologies, Beverly, Mass. or Millipore, Billerica, Mass.) that served as protein loading controls.

Quantitation of MBP expression, as shown in FIG. 4B, was performed with densitometry of the bands in each lane, and each lane represented an individual animal. The graphs represent the average intensity of MBP expression normalized by the corresponding actin signal in relative fluorescence units (Normalized R.F.U.). One-way analysis of variance (ANOVA) detected a significant increase the expression of both 18 kDa MBP ($F[3.32]=3.187$; $p=0.037$; Power=0.681) and 21 kDa MBP ($F[3.32]=4.270$; $p=0.012$; Power=0.816) with NANA supplementation. In addition, Tukey's post hoc test detected that the lactational diet significantly increased the expression of both MBP isoforms (*, $p<0.05$) compared to the NANA-deficient diet in the overall analysis as well as at postnatal day 8.

Example 3

Maternal Feeding of NANA During Gestation and Lactation Increases Neurite Extension in Hippocampal Cultures in Offspring The hippocampus is a specific region of the brain that is essential for spatial learning and for moving short-term memories into long-term memory. Neurite extension in cultures of the hippocampus serves as a measure of brain cell growth, differentiation, and networking. Increases in these ex vivo measures are considered beneficial because it is believed that similar beneficial processes occur in vivo.

Figure 5A:
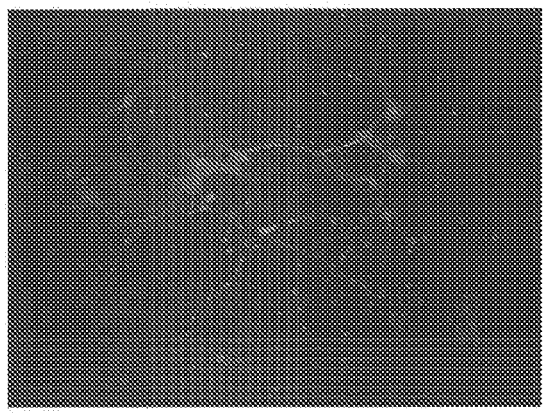
FIGS. 5A-5C and 6A-6B show the effects of maternal sialic acid supplementation on neurite extension in cultures of hippocampal cells derived from the offspring.
Figure 5B:
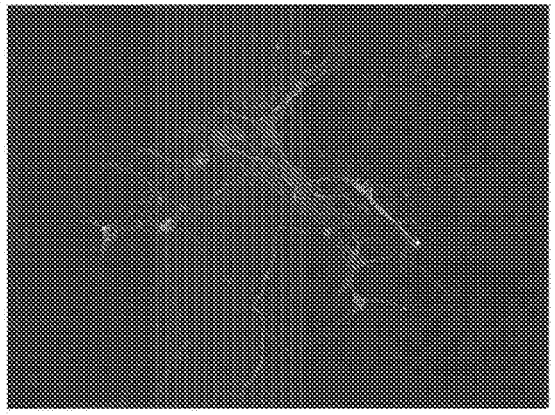

To determine the effects of maternal NANA supplementation on the brain development of offspring, neurite extension was measured in hippocampal cultures made from p0 pups described in FIG. 2. FIG. 5A shows the measurements of offspring of dams exposed to a NANA-deficient diet during gestation. FIG. 5B shows the measurements of offspring of dams that were fed a NANA-supplemented (200 mg/kg/d) diet during gestation. After 6 days of incubation the cultures underwent immunocytochemistry for the neuron-specific marker, Map2a (Sigma, Ronkonkoma, N.Y.; or Millipore, Billerica, Mass.). The number of cells in each culture was assessed by staining with 4',6-diamidino-2-phenylindole (DAPI).

Figure 5C:
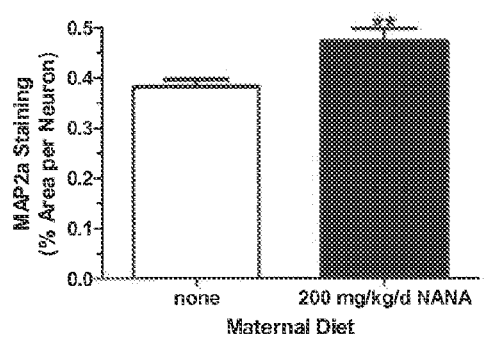

As shown in FIG. 5C, quantitation of the percent area of Map2a staining per neuron was significantly greater in cultures derived from pups whose mothers had received NANA in their diets. The percent area of Map2a staining was determined by computerized counting of all Map2a positive pixels in each image (5 random fields for each of 9-10 cultures per group; 1 culture per animal). The number of Map2a positive pixels in an image was then divided by the total number of pixels in that same image. The resulting quotient was then multiplied by 100 to yield percent (%) area. The percent area was then divided by the total number of cells in the image in order to normalize for cell number. A two-tailed, unpaired students t-test was used to compare the two groups, and the test detected a significant difference between the supplemented group and the control group (**, $p<0.01$). Thus, maternal exposure to NANA significantly increased neurite extension in hippocampal cultures of the offspring.

Example 4

Figure 6A:
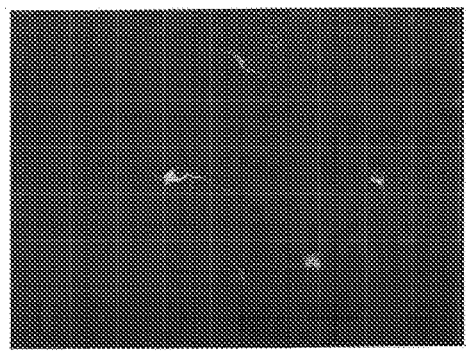
Figure 6A:
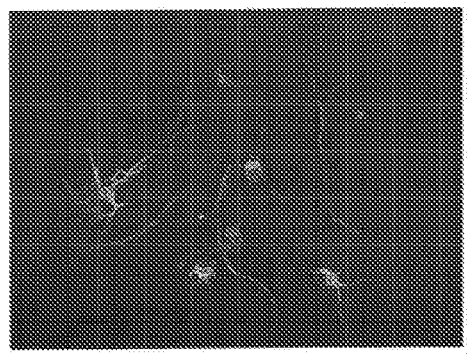
Figure 6A:
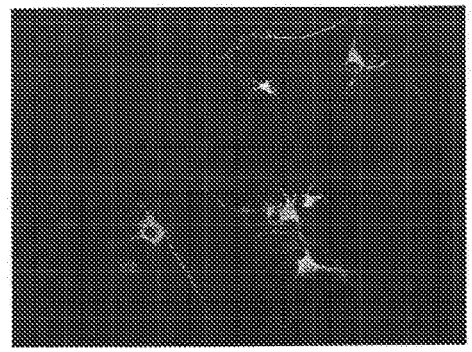
Figure 6A:
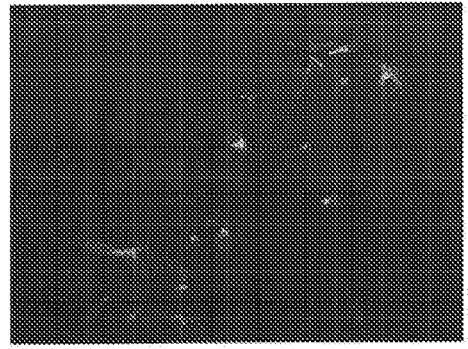
Figure 6A:
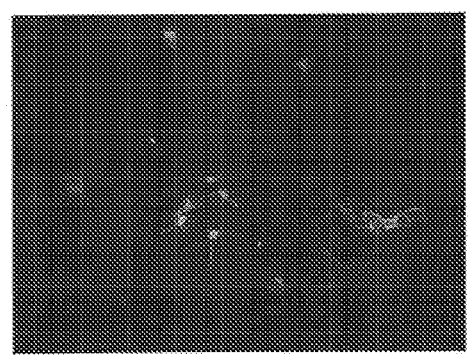

Maternal Feeding of Varying NANA Doses During Gestation Enhances the Neurite Extension in the Offspring To further assess the dose-response effects of maternal NANA supplementation during gestation on the brain development of offspring, neurite extension was measured in hippocampal cultures made from pups described in FIG. 3A. FIG. 6A shows representative hippocampal cultures derived from offspring of dams having a NANA-deficient diet during gestation ("no NANA") or a NANA-supplemented (25 mg/kg/d NANA, 50 mg/kg/d NANA, 100 mg/kg/d NANA, and 200 mg/kg/d NANA) diet during gestation. After 6 days of incubation, the cultures underwent immunocytochemistry for the neuron-specific marker, Map2a (Sigma, Ronkonkoma, N.Y.; or Millipore, Billerica, Mass.). The number of cells in each culture was assessed by staining with 4',6-diamidino-2-phenylindole (DAPI).

Figure 6B:
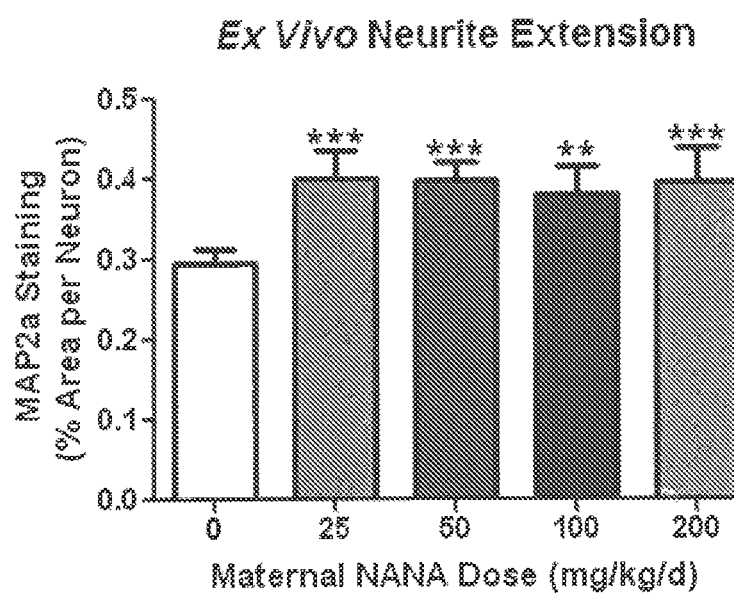

The percent area of Map2a staining per neuron was quantitated as described in Example 3. As shown in FIG. 6B, the percent area of Map2a staining per neuron was significantly greater in cultures derived from pups whose mothers had received NANA in their diets (, $p<0.01$; *, $p<0.001$). Thus, maternal exposure to NANA significantly increased neurite extension in hippocampal cultures of the offspring.

Example 5

Figure 7A:
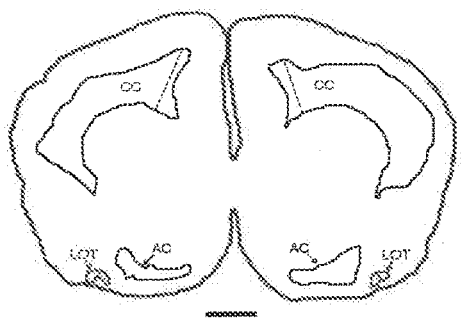
FIGS. 7A-7C, 8A-8D, 9A-9B, 10A-10D, 11A-11B and 12A-12B show the effects of sialic acid supplementation on the thickness (FIGS. 7-11) or levels (FIG. 12) of MBP expression in specific regions of the developing rat brain.

Maternal Feeding of NANA During Gestation and Lactation Increases the Thickness of MBP Expression in White Matter Increased thickness and maturity of the myelin sheath is associated with faster conduction velocities and more advanced development and differentiation of white matter (myelinated brain areas). In particular, the corpus callosum (CC) is the major tract for communication between the two cerebral hemispheres that control executive function and learning. Also, the lateral olfactory tract (LOT) is particularly important in rodents because they rely largely on their olfactory system for orientation and food-guided behavior in their normal environments. The LOT carries information from the primary olfaction centers of the olfactory bulbs to higher processing centers in the cerebrum and hippocampus. The CC and LOT were measured in the following experiments because of their size and because of their importance in brain function and in the animals' abilities to sense their environments To determine the effects of maternal NANA supplementation on the brain development of offspring, assessment of the CC and LOT was performed by taking thin slices of the p16 pup brain described in FIG. 2, staining the slices with MBP immunohistochemistry, and measuring the areas of interest with confocal laser microscopy. As shown in FIG. 7A, the thickness of MBP expression in the CC was measured at the cingulum (dashed line) in rostral (less developed) and midline (more developed) areas of the brain (scale bar=1 millimeter). The locations of the LOT and regions associated with the anterior commissure (AC) are also illustrated in FIG. 7A.

Figure 7B:
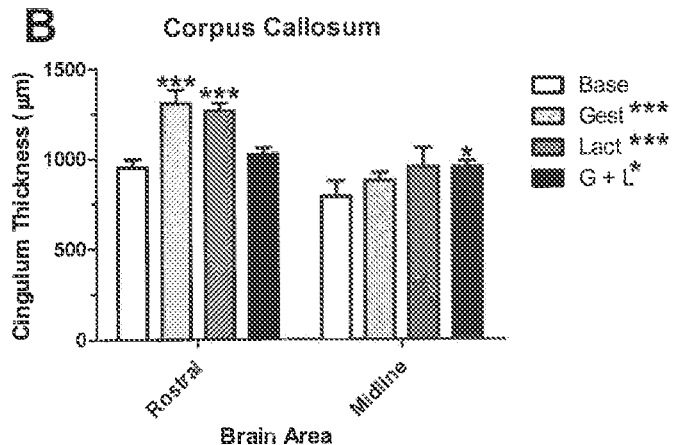
Figure 7C:
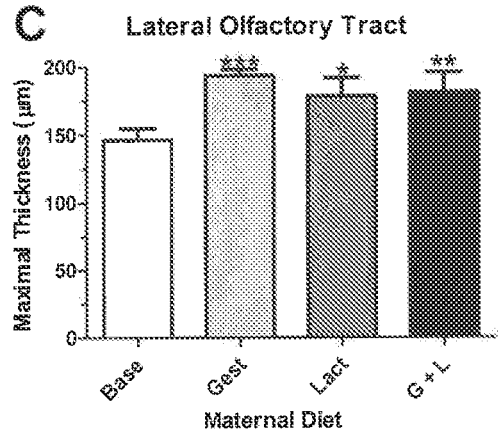

FIG. 7B shows maternal NANA supplementation during gestation (Gest), lactation (Lact), or gestation plus lactation (G+L) (as described in FIG. 2) resulted in significant increases [multivariate ANOVA; F[3.86]=8.455; p<0.001] to the thickness of MBP expression in the CC in the offspring (p<0.05; , p<0.01; and *, p<0.001). FIG. 7C shows maternal NANA supplementation also resulted in significant increases to the maximal thickness of MBP expression in the LOT which were similar to those detected in the CC. Furthermore, these findings were consistent with the Western blot findings described in Example 2.

Example 6

Maternal Feeding of Varying NANA Doses During Gestation Increases the Thickness of MBP Expression in White Matter To further assess the effects of maternal NANA supplementation during gestation on the brain development of offspring, assessment of the corpus callosum (CC) and lateral olfactory tract (LOT) was performed by taking thin slices of the p16 pup brain (GestDR p16) described in FIG. 3A, staining the slices with MBP immunohistochemistry, and quantitating the areas of interest with confocal laser microscopy as described in Example 2. Maternal supplementation with NANA at doses of 25 mg/kg/d, 50 mg/kg/d, 100 mg/kg/d and 200 mg/kg/d was tested.

Figure 8A:
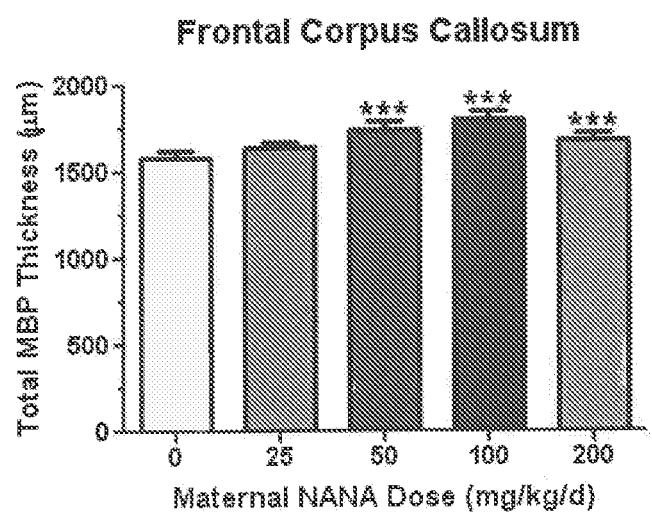
Figure 8B:
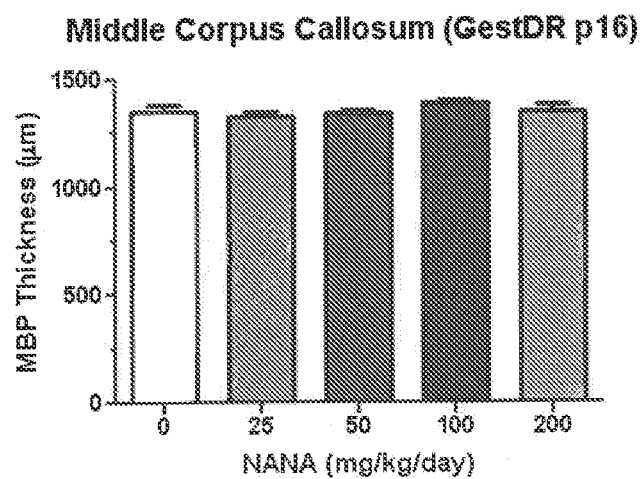
Figure 8C:
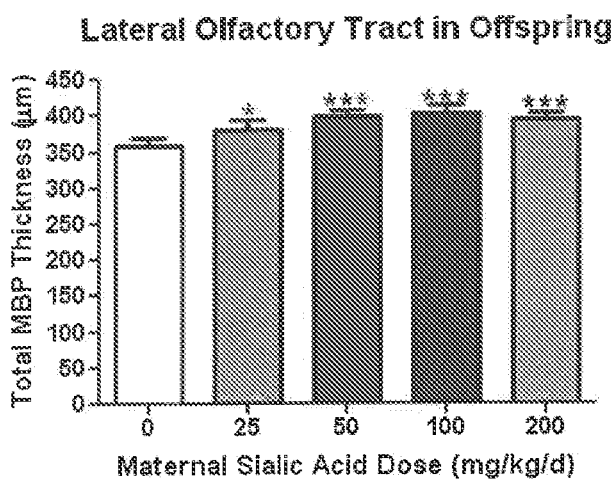
Figure 8D:
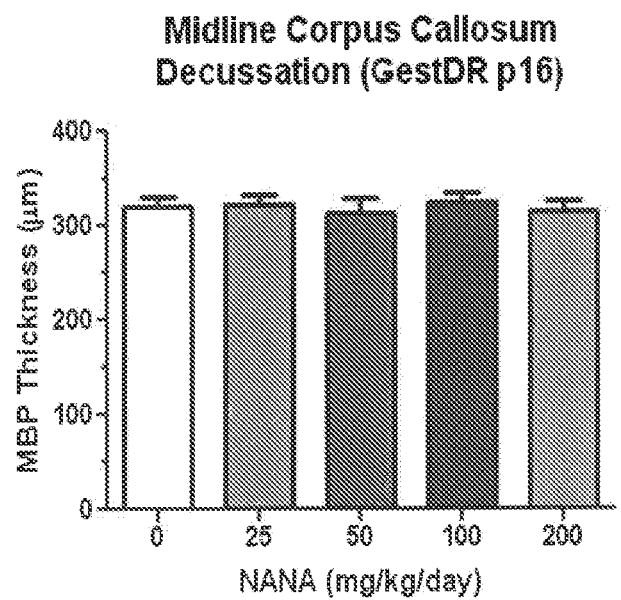

FIG. 8A shows maternal NANA supplementation during gestation resulted in significant increases to the thickness of MBP expression in the frontal CC in the offspring (***, p<0.001). FIG. 8B shows maternal NANA supplementation did not appear to change the thickness of MBP expression in the middle CC. FIG. 8C shows maternal NANA supplementation resulted in significant increases to the thickness of MBP expression in the LOT (*, p<0.05; ***, p<0.001). FIG. 8D shows maternal NANA supplementation did not appear to change the thickness of MBP expression in the midline CC decussation.

Example 7

Maternal Feeding of Varying NANA Doses During Gestation Increases MBP Expression in Motor Output and Sensory Input Pathways The white matter of the spinal cord contains tracts of fibers that are ascending (sensory) or descending (motor). The ascending tracts convey sensory information from cutaneous receptors, proprioceptors (muscle and joint senses) and visceral receptors. The medial lemniscus is a pathway that carries such sensory information from the gracile and cuneate nuclei to the thalamus. There are two major descending tracts: the corticospinal, or pyramidal tract, and the extrapyramidal tract. In general, these tracts are involved in the control of the musculature of the body.

To further assess the effects of maternal NANA supplementation during gestation on the brain development of offspring, assessment of the motor pyramids and medial lemniscus was performed by taking thin slices of the p16 pup brain described in FIG. 3A, staining the slices with MBP immunohistochemistry, and quantitating the areas of interest with confocal laser microscopy as described in Example 2. Maternal supplementation with NANA at doses of 25 mg/kg/d, 50 mg/kg/d, 100 mg/kg/d and 200 mg/kg/d was tested.

Figure 9A:
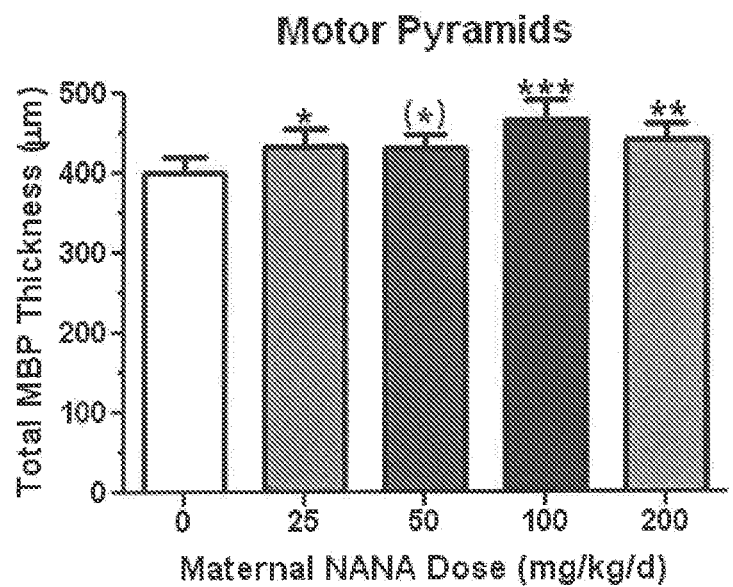
Figure 9B:
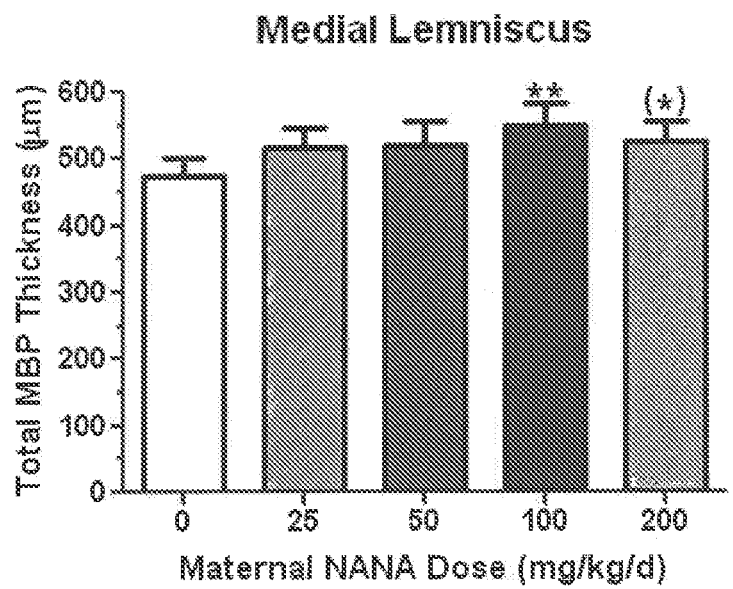

FIG. 9A shows maternal NANA supplementation during gestation resulted in significant increases to the thickness of MBP expression in the motor pyramids in the offspring (*, p<0.05; , p<0.01; *, p<0.001). FIG. 9B shows maternal NANA supplementation resulted in significant increases to the thickness of MBP expression in the medial lemniscus (*, p<0.05; **, p<0.01).

Example 8

Maternal Feeding of Varying NANA Doses During Lactation Increases the Thickness of MBP Expression in White Matter To further assess the effects of maternal NANA supplementation during lactation on the brain development of offspring, assessment of the corpus callosum (CC) and lateral olfactory tract (LOT) was performed by taking thin slices of the p16 pup brain (LacDR p16) described in FIG. 3B, staining the slices with MBP immunohistochemistry, and quantitating the areas of interest with confocal laser microscopy as described in Example 2. Maternal supplementation with NANA at doses of 25 mg/kg/d, 50 mg/kg/d, 100 mg/kg/d and 200 mg/kg/d was tested.

Figure 10A:
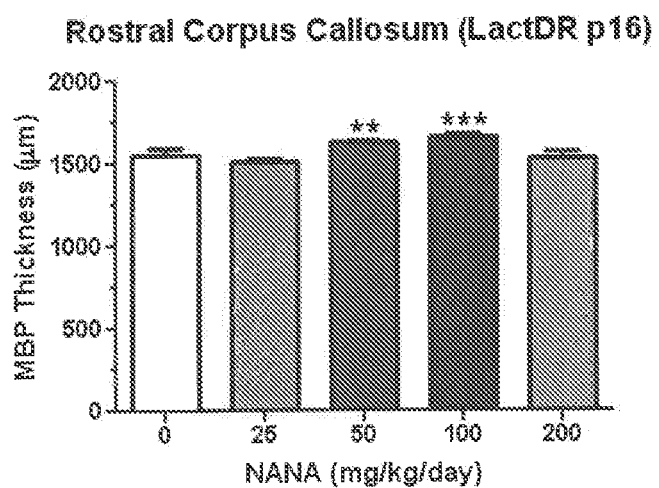
Figure 10B:
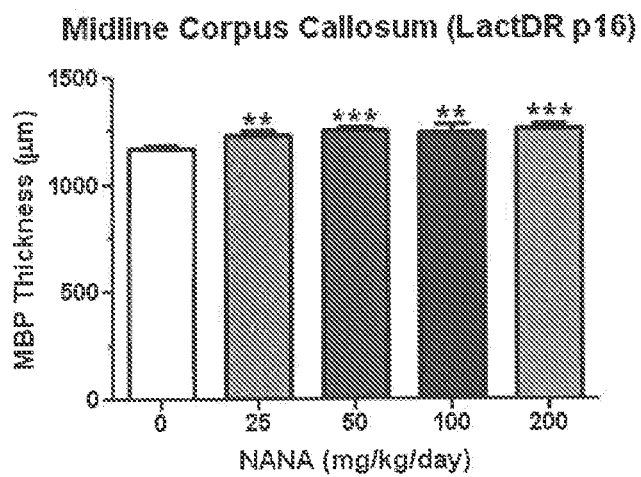
Figure 10C:
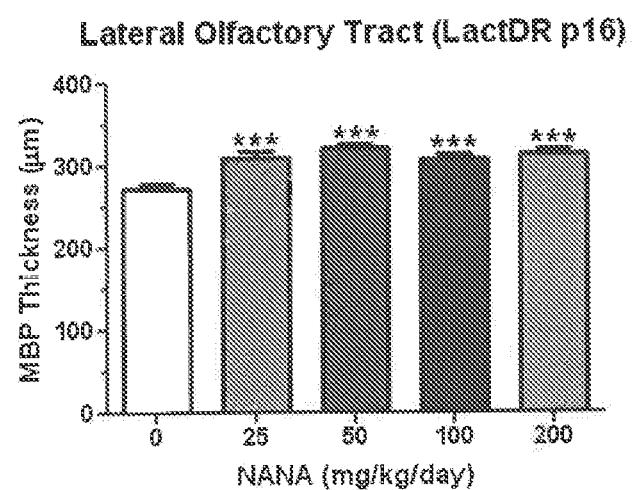
Figure 10D:
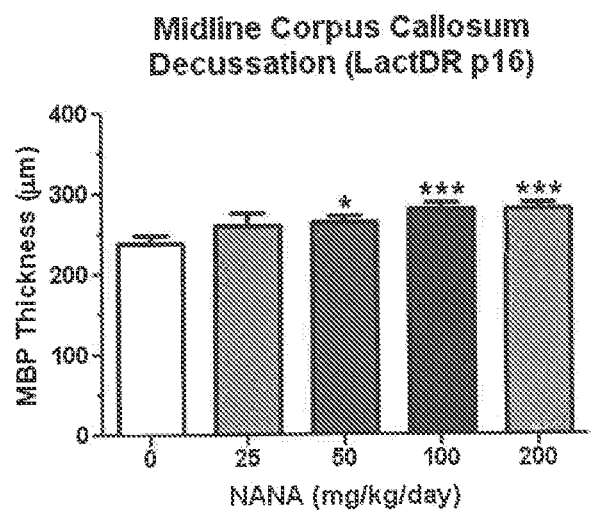

FIG. 10A shows maternal NANA supplementation during lactation resulted in significant increases to the thickness of MBP expression in the rostral CC in the offspring (, p<0.01; *, p<0.001). FIG. 10B shows maternal NANA supplementation during lactation resulted in significant increases to the thickness of MBP expression in the midline CC in the offspring (, p<0.01; *, p<0.001). FIG. 10C shows maternal NANA supplementation during lactation resulted in significant increases to the thickness of MBP expression in the LOT in the offspring (***, p<0.001). FIG. 10D shows maternal NANA supplementation during lactation resulted in significant increases to the thickness of MBP expression in the midline CC decussation in the offspring (*, p<0.05; ***, p<0.001).

Example 9

Maternal Feeding of Varying NANA Doses During Lactation and MBP Expression in Motor Output and Sensory Input Pathways To further assess the effects of maternal NANA supplementation during lactation on the brain development of offspring, assessment of the motor pyramids and medial lemniscus was performed by taking thin slices of the p16 pup brain (LacDR p16) described in FIG. 3B, staining the slices with MBP immunohistochemistry, and quantitating the areas of interest with confocal laser microscopy as described in Example 2. Maternal supplementation with NANA at doses of 25 mg/kg/d, 50 mg/kg/d, 100 mg/kg/d and 200 mg/kg/d was tested.

Figure 11A:
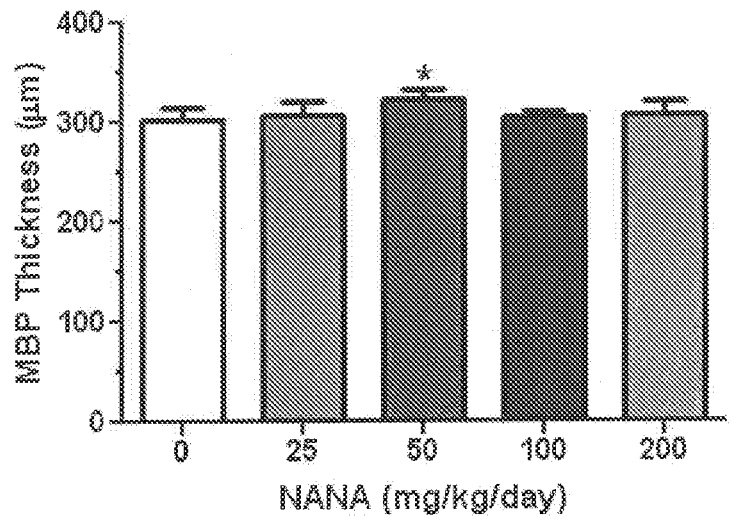
Figure 11B:
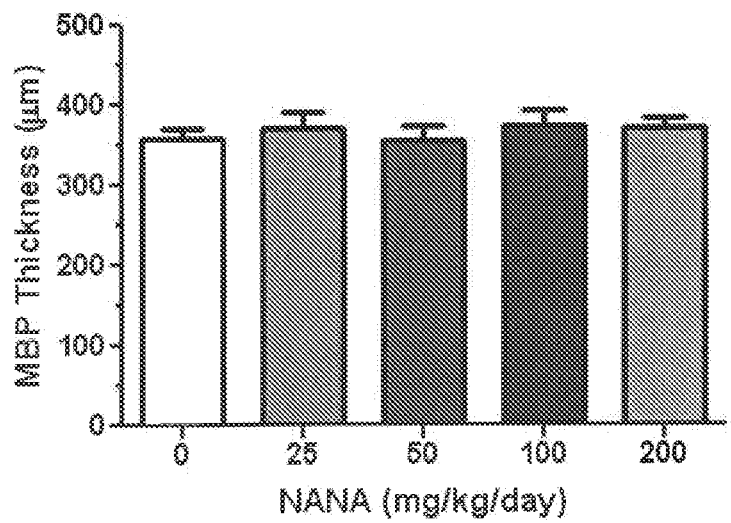

FIG. 11A shows maternal NANA supplementation during lactation resulted in a significant increase to the thickness of MBP expression in the motor pyramids following maternal supplementation with NANA at a dose of 50 mg/kg/d in the offspring (*, p=0.022) and no significant changes to the thickness of MBP expression in the motor pyramids following maternal supplementation with NANA at the other doses tested. FIG. 11B shows maternal NANA supplementation during lactation resulted in no significant changes to the thickness of MBP expression in the medial lemniscus in the offspring.

Example 10

Maternal Feeding of Varying NANA Doses During Lactation Increases MBP Expression in the Cerebellum To further assess the effects of maternal NANA supplementation during lactation on the brain development of offspring, MBP expression was measured by western blot analysis of cerebellum that was harvested from pups at postnatal days 0, 8, and 16 described in FIG. 3B. As described in Example 2, the blots were probed with an antibody for MBP as described in Example 2 that recognizes the 18 kilodalton form (18 kD MBP) and 21 kilodalton form (21 kD MBP) and an antibody for β-actin as a protein loading control. Quantitation of MBP expression performed with densitometry of the bands in each lane, and each lane represented an individual animal as described in Example 2.

Figure 12A:
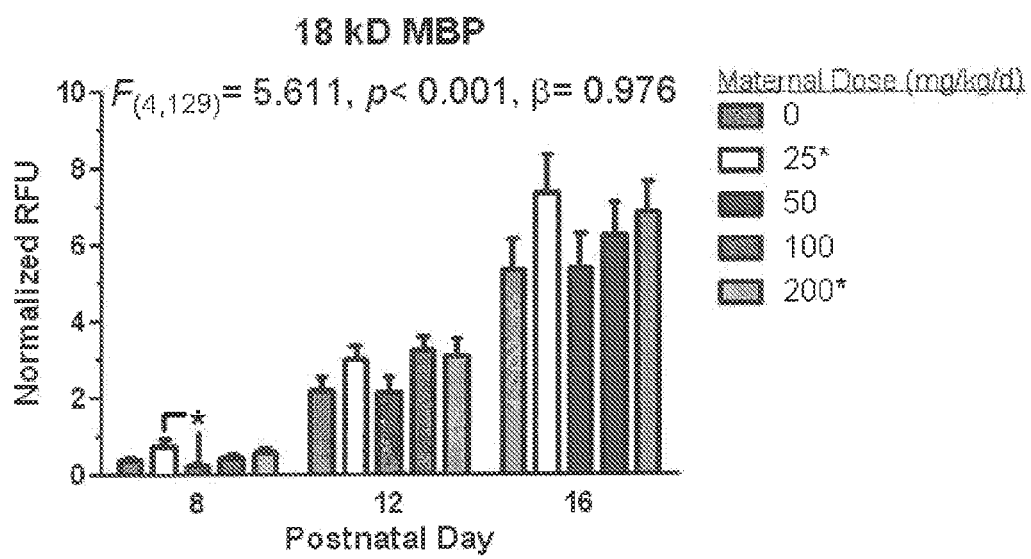
Figure 12B:
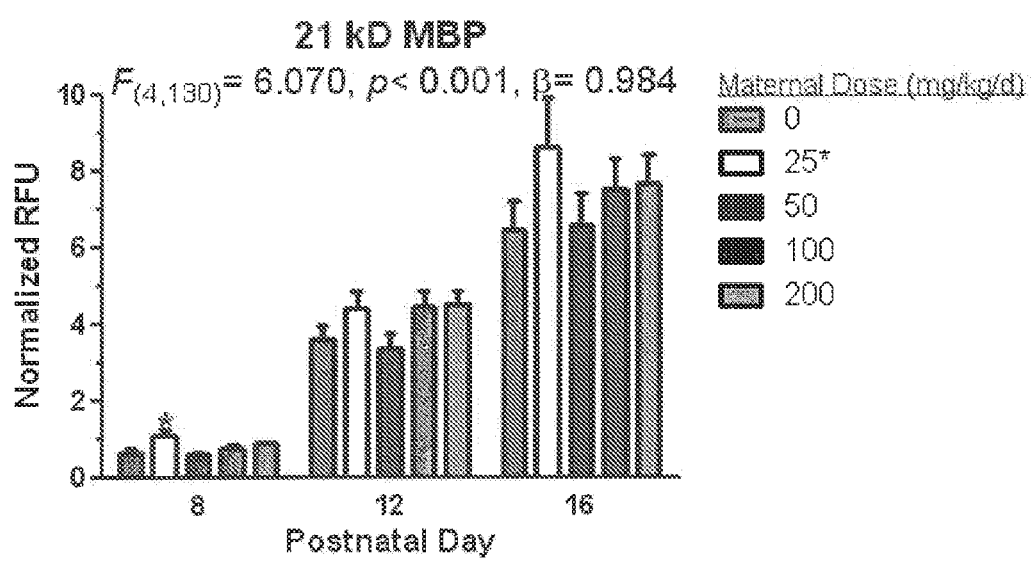

The graphs in FIGS. 12A and 12B represent the average intensity of MBP expression normalized by the corresponding actin signal in relative fluorescence units (Normalized R.F.U.). One-way analysis of variance (ANOVA) detected a significant increase the expression of both 18 kDa MBP and 21 kDa MBP with NANA supplementation during lactation at certain doses tested ($p<0.001$).

Analysis of the combined expression intensities of 18 kDa MBP and 21 kDa MBP showed a significant increase in total MBP following NANA supplementation during lactation at NANA doses of 25 mg/kg/d ($p<0.01$), 100 mg/kg/d ($p<0.05$), and 200 mg/kg/d ($p<0.01$).

Example 11

NANA Crosses the Blood-Brain-Barrier and is Partially Converted to Neu5Gc in Non-Human Animals To assess whether NANA is bioavailable to the brain in its native form or whether NANA is processed on its way across the blood-brain barrier, the levels of NANA and one of its potential metabolites were measured in rat cerebrospinal fluid (CSF). The animals' diets were first cleared of NANA by placing them on NANA-free diets for one week. The animals were then given a single, oral dose of NANA (200 mg/kg), and the CSF of each animal was sampled at 0, 0.25, 1, 2, 4, and 6 hours after dosing. The concentrations of NANA and Neu5Gc in the CSF were then assessed by high-pressure liquid chromatography coupled with fluorescence detection methods and quantitation standards.

FIG. 13 illustrates the changes in the concentrations of NANA and Neu5Gc in the CSF after oral NANA dosing. As FIG. 13A shows, a peak of native NANA was detectable above baseline 15 minutes after dosing. This NANA peak then decayed relatively rapidly and returned to baseline values by 1 hour after oral NANA dosing. These data suggest that native NANA crossed the blood-brain barrier as a result of the exogenous dosing. NANA was then either absorbed into the brain tissue itself, processed into metabolites such as Neu5Gc or ManNAc, or both. Indeed, as FIG. 13B shows, at least some of the NANA was likely being converted to Neu5Gc. The Neu5Gc concentrations did not increase above baseline until 1 hour after oral dosing, and this increase was noticeably after the NANA peak observed at 15 minutes after dosing. The Neu5Gc concentrations were then sustained throughout the rest of the sampling period at levels that were approximately 4% of the peak NANA concentration. Thus, exogenous NANA is bioavailable to the brain, but it is also processed to some extent. It should be noted here that, unlike all other mammals, humans do not possess a functional enzyme for converting NANA to Neu5Gc, so the data would likely be different in human CSF.

The foregoing description of the invention has been presented for purposes of illustration and description. Furthermore, the description is not intended to limit the invention to the form disclosed herein.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A method for providing sialic acid to a female, wherein the sialic acid is in the form of n-acetylneuraminic acid, comprising administering sialic acid to the female during at least one of the stages of preconception, pregnancy and lactation,
   wherein the sialic acid provides a developmental benefit to a fetus or child of the female.

2. The method of claim 1, wherein the sialic acid is a free sialic acid.

3. The method of claim 1, wherein the sialic acid is a sialic acid precursor that is metabolized into sialic acid.

4. The method of claim 1, wherein the sialic acid is administered during pregnancy and lactation.

5. The method of claim 1, wherein the sialic acid is administered during preconception, pregnancy and lactation.

6. The method of claim 1, wherein the sialic acid is administered to the female during the first two years following birth of a child by the female.

7. The method of claim 1, wherein the developmental benefit is improved development of the nervous system and/or brain.

8. The method of claim 1, wherein the developmental benefit is a neurological improvement of the brain.

9. The method of claim 1, wherein the developmental benefit is selected from the group consisting of: increased expression and/or development of mature myelin, enhanced neurite extension, increased levels of myelin basic protein, enhanced development the white matter of the brain, and combinations thereof.

10. The method of claim 1, wherein the developmental benefit is in the gray matter of the brain.

11. The method of claim 1, wherein the sialic acid is administered in a dosage form.

12. The method of claim 11, wherein the dosage form is selected from the group consisting of: nutritional supplement, food, pharmaceutical formulation, beverage, and combinations thereof.

13. The method of claim 11, wherein the dosage form contains sialic acid at an amount of 0.01% to 10% by weight of the dosage form.

14. The method of claim 11, wherein the dosage form contains sialic acid at an amount of 10% to 90% by weight of the dosage form.

15. The method of claim 1, wherein the sialic acid is administered at an amount of 5 mg/kg/day to 200 mg/kg/day of the female's body weight.

16. The method of claim 15, wherein the sialic acid is administered at an amount of 25 mg/kg/day to 100 mg/kg/day of the female's body weight.

17. The method of claim 1, wherein the sialic acid is administered at an amount of 20 mg/day to 4000 mg/day.

18. The method of claim 17, wherein the sialic acid is administered at an amount of 200 mg/day to 2000 mg/day.

19. The method of claim 1, further comprising administering to the female one or more polyunsaturated fatty acids, calcium, folic acid, vitamin B, tocotrienols, vitamin D, magnesium, phosphorus, vitamin K, iron, vitamin B12, niacin, thiamine, riboflavin, biotin, vitamin B6, and isoflavones, zinc, pantothenic acid, medium chain triglycerides, copper, manganese, magnesium, vitamin A, choline, vitamin C, iodine, selenium, prebiotics, probiotics, beta-carotene, lutein, lycopene, alpha-carotene, zeaxanthin, beta-cryptoxanthin, gamma carotene, ginger, and tryptophan.

* * * * *